(12) United States Patent
Tribble et al.

(10) Patent No.: US 10,383,568 B2
(45) Date of Patent: Aug. 20, 2019

(54) CONFIRMING SLEEP BASED ON SECONDARY INDICIA OF USER ACTIVITY

(71) Applicant: Apple Inc., Cupertino, CA (US)

(72) Inventors: Guy L. Tribble, Cupertino, CA (US); Roy J. Raymann, Cupertino, CA (US); Wren N. Dougherty, Cupertino, CA (US); Divya Nag, Cupertino, CA (US); Deborah M. Lambert, Cupertino, CA (US); Stephanie Greer, Cupertino, CA (US); Thomas R. Gruber, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 548 days.

(21) Appl. No.: 14/871,887

(22) Filed: Sep. 30, 2015

(65) Prior Publication Data

US 2017/0086732 A1  Mar. 30, 2017

(51) Int. Cl.
*A61B 5/00* (2006.01)
*A61B 5/11* (2006.01)

(52) U.S. Cl.
CPC ............ *A61B 5/4809* (2013.01); *A61B 5/002* (2013.01); *A61B 5/0022* (2013.01); *A61B 5/1118* (2013.01); *A61B 5/681* (2013.01); *A61B 5/6803* (2013.01); *A61B 5/746* (2013.01)

(58) Field of Classification Search
CPC .................................................. A61B 5/4809
See application file for complete search history.

(56) References Cited

U.S. PATENT DOCUMENTS

| | | |
|---|---|---|
| 6,999,791 B1 | 2/2006 | Ishikura et al. |
| 2008/0062291 A1 | 3/2008 | Sako et al. |
| 2008/0146892 A1* | 6/2008 | LeBoeuf .............. A61B 5/0205 600/300 |
| 2014/0247208 A1 | 9/2014 | Henderek et al. |

FOREIGN PATENT DOCUMENTS

| | | | |
|---|---|---|---|
| GB | 2460580 | 7/2010 | |
| WO | 2012 058886 A1 | 10/2012 | |
| WO | WO 2013086363 A2 * | 6/2013 | ............. A61B 5/002 |

* cited by examiner

*Primary Examiner* — Sean P Dougherty
*Assistant Examiner* — Nicholas E Kolderman
(74) *Attorney, Agent, or Firm* — Invoke

(57) ABSTRACT

In some implementations, a computing device can confirm a sleep determination for a user based on secondary indicia of user activity. For example, the computing device can be a user's primary computing device. The primary device can predict and/or determine when the user is sleeping based on the user's use (e.g., primary indicia), or lack of use, of the primary device. After the primary device determines that the user is sleeping, the primary device can confirm that the user is asleep based on secondary indicia of user activity. In some implementations, the secondary indicia can include user activity reported to the primary computing device by other secondary computing devices (e.g., a second user device, a household appliance, etc.). In some implementations, the secondary indicia can include user activity detected by sensors of the primary computing device (e.g., sound, light, movement, etc.).

24 Claims, 7 Drawing Sheets

CONFIRMING SLEEP BASED ON SECONDARY INDICIA OF USER ACTIVITY

TECHNICAL FIELD

The disclosure generally relates to determining when a user is sleeping.

BACKGROUND

Mobile computing devices are ubiquitous in the modern world. People are constantly using their smartphones, tablet computers, and/or other portable devices. These devices can track when the user is using the device, the location where the user is using the device, environmental conditions around the device, and/or other indicia of use. The computing devices can analyze this usage data (e.g., indicia of use) and determine various behaviors or patterns of activity associated with the user of the device. For example, a user's pattern of use of a device (e.g., a smartphone) can be analyzed to predict the user's sleep period patterns and/or detect when a user is sleeping. However, if a user uses multiple computing devices, the sleep prediction and/or sleep detection performed by the user's primary computing device may be erroneous.

SUMMARY

In some implementations, a computing device can confirm a sleep determination for a user based on secondary indicia of user activity. For example, the computing device can be a user's primary computing device. The primary device can predict and/or determine when the user is sleeping based on the user's use (e.g., primary indicia), or lack of use, of the primary device. After the primary device initially determines that the user is sleeping, the primary device can confirm that the user is asleep based on secondary indicia of user activity. In some implementations, the secondary indicia can include user activity reported to the primary computing device by other secondary computing devices (e.g., a second user device, a household appliance, etc.). In some implementations, the secondary indicia can include user activity detected by sensors of the primary computing device (e.g., sound, light, movement, etc.).

Particular implementations provide at least the following advantages: sleep predictions can become more accurate by including secondary indicia in the sleep predication algorithm; sleep detection can become more accurate by accounting for user activity not associated with the primary device.

Details of one or more implementations are set forth in the accompanying drawings and the description below. Other features, aspects, and potential advantages will be apparent from the description and drawings, and from the claims.

DESCRIPTION OF DRAWINGS

Like reference symbols in the various drawings indicate like elements.

DETAILED DESCRIPTION

Figure 1:
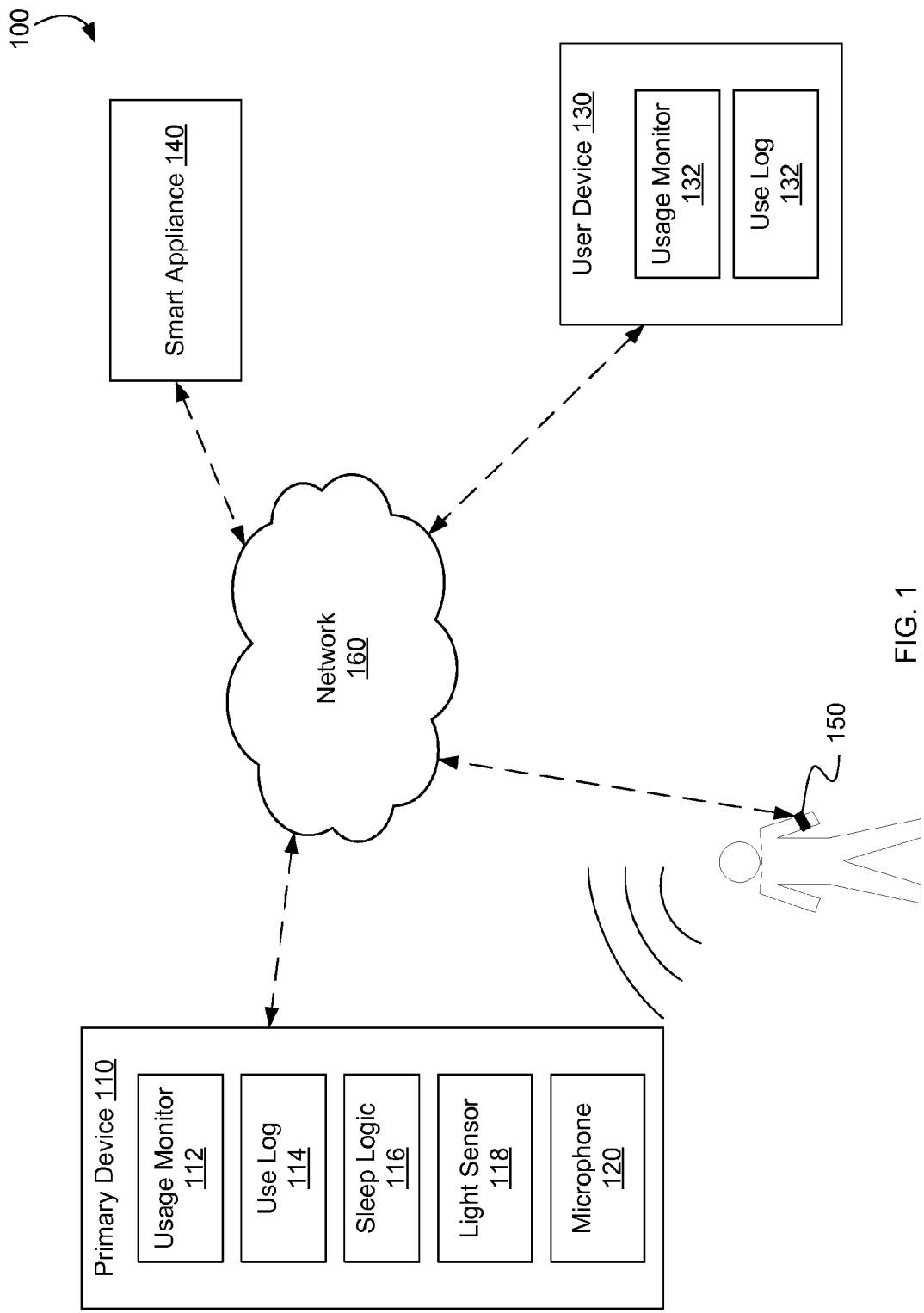
FIG. 1 is a block diagram of an example system for confirming sleep based on secondary indicia of user activity.

FIG. 1 is a block diagram of an example system 100 for confirming sleep based on secondary indicia of user activity. System 100 can include primary device 110. For example, primary device 110 can be a user's primary computing device (e.g., the computing device that the user uses most often). Primary device 110 can be a smartphone, a tablet computer, a smart watch, or any other computing device.

In some implementations, primary device 110 can include usage monitor 112. For example, usage monitor 112 can monitor the user's use of primary device 110. Usage monitor 112 can detect when the user turns on primary device 110, for example. Usage monitor 112 can detect when the display of primary device 110 is illuminated. Usage monitor 112 can detect when the user provides input to primary device 110, and/or uses an application installed on primary device 110. Usage monitor 112 can detect when the user stops using primary device 110. For example, usage monitor 112 can detect when the user puts primary device 110 into a sleep mode, low power mode, or turns primary device 110 off. Usage monitor can record the user's use of primary device 110 over time in use log 114 (e.g., database or log file) stored on primary device 110, for example.

In some implementations, primary device 110 can include sleep logic 116. For example, sleep logic 116 can be a software process (e.g., application, operating system utility, operating system daemon, etc.) running on primary device 110. In some implementations, sleep logic 116 can analyze the historical data in use log 114 to predict when a user will sleep. For example, sleep logic 116 can determine when a user was sleeping in the past by identifying periods of time (e.g., greater than 5 hours, greater than 6 hours, etc.) when the user was not using primary device 110. The user's intentional (e.g., deliberate, active, not passive) use of primary device 110 can be the primary indicia of user activity, for example. Sleep logic 116 can, for example, determine a pattern of sleep periods over a number of days or weeks. For example, based on the historical data in use log 114, sleep logic 116 can determine that the user typically sleeps between 11 pm and 6 am. Sleep logic 116 can predict future sleep periods based on the sleep period patterns derived from the historical data in use log 114. For example, if the user historically sleeps between 11 pm and 6 am, sleep logic 116 can predict that the user will go to sleep at 11 pm and wake at 6 am in the future.

In some implementations, sleep logic 116 can determine sleep period patterns based on a single usage statistic. For example, sleep logic 116 can analyze display illumination statistics to determine when primary device 110 is being used by the user and when the user is asleep or awake. For example, if the display is illuminated, primary device 110 is in use, and the user is awake. If the display is dark (not illuminated), then primary device 110 is not being used. If primary device 110 has not been used for a period of time (e.g., at least 5 hours), then sleep logic 116 can determine that the user is asleep.

In some implementations, sleep logic 116 can determine sleep period patterns based on multiple usage statistics. For example, in addition display illumination statistics, sleep logic 116 can determine when the user is sleeping based on use of a headphone jack. For example, the display may be dark but the user might be listening to music through headphones connected to primary device 110. Thus, sleep logic 116 can determine that the user is awake even though the display is dark.

In some implementations, sleep logic 116 can confirm that the user is sleeping (or awake) based on secondary indicia of user activity. For example, when sleep logic 116 determines that a user is sleeping using the primary indicia of user activity described above, sleep logic 116 can monitor secondary indicia of user activity to confirm that the user is sleeping. For example, sleep logic 116 can provisionally determine that the user is sleeping based on primary indicia of user activity and confirm (or disprove) the user is sleeping based on secondary indicia of user activity. The secondary indicia of user activity can correspond to conscious human activity that indicates the user is awake, for example.

In some implementations, the secondary indicia of user activity can be passively detected by primary device 110 using sensors built in to or connected to primary device 110. For example, sleep logic 116 can activate or turn on various sensors of primary device 110 when sleep logic 116 has determined (e.g., provisionally determined) that the user is sleeping in order to detect the secondary indicia of user activity. In some implementations, primary device 110 can include light sensor 118 that can detect ambient light around primary device 110. For example, when the light sensor detects a high light level (e.g., above a threshold level) that indicates a bright room, sleep logic 116 can determine that the user is awake because most people do not sleep in well-lit rooms.

In some implementations, primary device 110 can include microphone 118 (e.g., sound sensor). Sleep logic 116 can use microphone 118 to detect sound associated with user activity. Sleep logic 116 can analyze patterns in the detected sound and determine particular user activities based on the sound patterns. For example, primary device 110 can obtain sound samples (e.g., fingerprints) from a sound database that are mapped to (correspond to) various human activities (e.g., walking, brushing teeth, closing blinds, etc.). The sound database can be stored on primary device 110 or stored on a remote server (not shown). Microphone 118 can detect sounds generated by a user (e.g., when the user is walking, brushing their teeth, closing the blinds, etc.) and compare the sounds to the sound samples obtained from the sound database to identify the human activity corresponding to the detected sound. If the detected sound can be matched to a human activity in the sound database, then sleep logic 116 can determine that the user is awake.

In some implementations, the secondary indicia of user activity can be received from secondary devices. For example, the secondary devices can be a user device 130 that the user uses less frequently than primary device 110. User device 130 can be, for example, a smartphone, tablet computer, laptop computer, or other computing device. The secondary device can be wearable device 150, such as a smartwatch or smart eye glasses. The secondary device can be smart appliance 140 (e.g., a smart refrigerator, a smart door lock, smart blinds, smart power grid, etc.). Each of these secondary devices can detect when the user is using the secondary device, or performing some other conscious human activity, and can report the activity to primary device 110. For example, the secondary devices (e.g., user device 130, smart appliance 140, wearable device 150, etc.) can report the user activity to primary device 110 through network 160 (e.g., a local area network, wide area network, Internet, home network, Wi-Fi network, Bluetooth network, etc.).

In some implementations, sleep logic 116 of primary device 110 can confirm that the user is asleep, or awake, based on the use statistics received from the secondary devices. For example, sleep logic 116 may initially determine that the user is asleep based on primary indicia of user activity, as described above. However, upon receiving secondary indicia of user activity from other devices, sleep logic 116 can determine that the user is actually awake. On the other hand, if sleep logic 116 does not receive any secondary indicia of user activity (e.g., from sensors or from other devices), sleep logic 116 can confirm that the user is asleep as initially determined.

Figure 2:
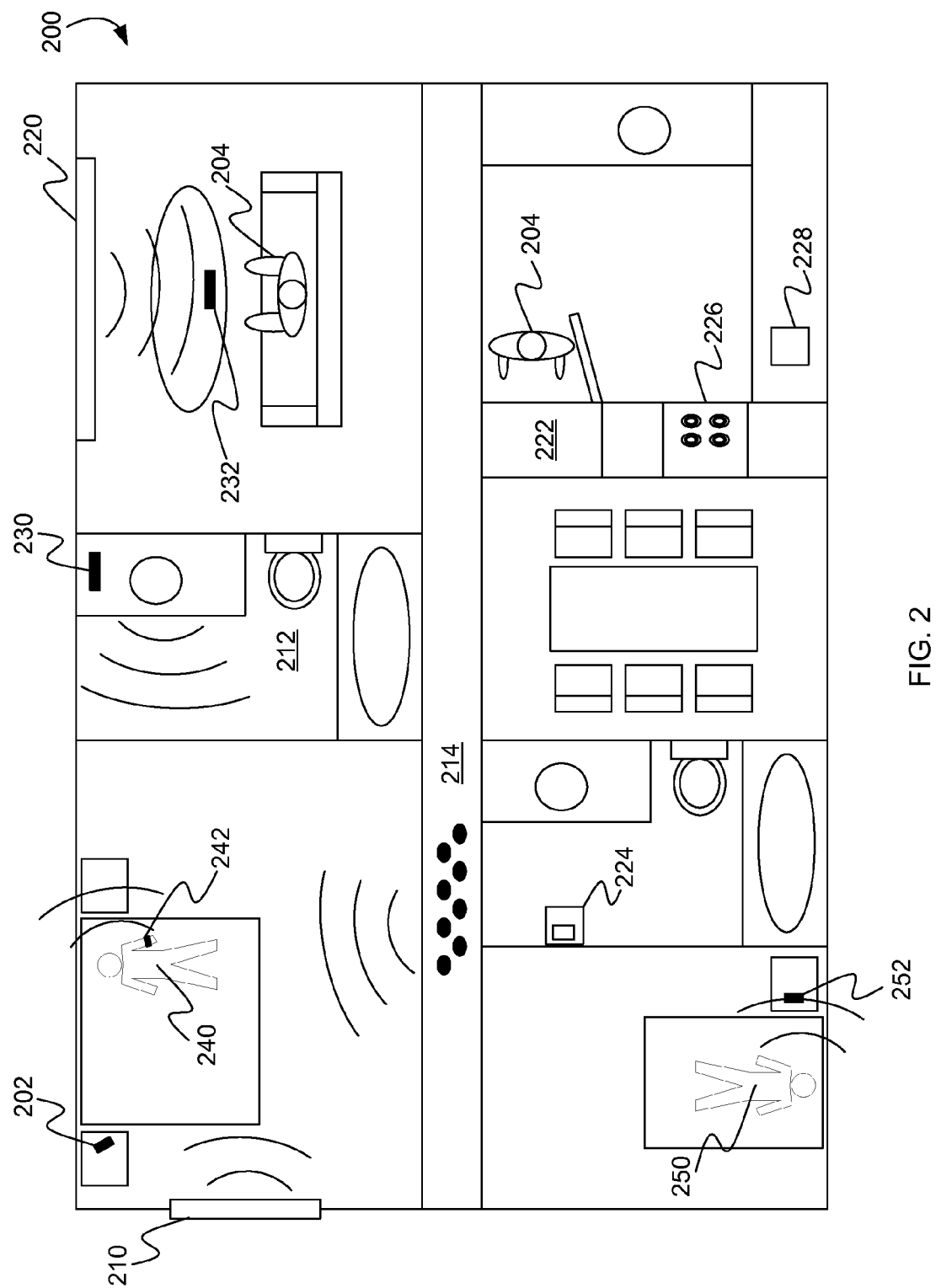
FIG. 2 is an illustration of examples of secondary indicia of user activity.

FIG. 2 is an illustration 200 of examples of secondary indicia of user activity. For example, secondary indicia of user activity can be generated from conscious human activity. Since sleeping usually occurs in the user's home, illustration 200 depicts the home environment and various sources of secondary indicia of user activity that can be generated in the home environment. Moreover, when users share the home environment with other people (e.g., family, roommates, etc.), the primary device will need to determine whether the conscious human activity is attributable to the user or other people in the home environment. For example, the primary device can eliminate other people as the source of the conscious human activity by determining that the other people in the house are asleep. The primary device can determine that the user is the source of the conscious human activity when the devices being used receive data (e.g., log in credentials, physical characteristics, media preferences, etc.) specific to the user.

In some implementations, primary device 202 can determine that user 204 is sleeping. For example, primary device 202 can correspond to primary device 110 of FIG. 1. In some implementations, primary device 202 can determine user 204 is sleeping based on primary indicia of user activity (e.g., user activity with respect to primary device 202), as described above. However, in some instances, user 204 may have just left primary device 202 on a table or nightstand while user 204 performs some other activity away from primary device 202. Primary device 202 may interpret the inactivity with respect to primary device 202 while primary device 202 is on the table as user 204 sleeping when user 204 is actually awake and active elsewhere.

Detecting Conscious Human Activity

In some implementations, primary device 202 can detect environmental conditions indicating that a human is awake. For example, the detected environmental conditions (e.g., sound, light, etc.) can be secondary indicia of user activity. In some implementations, primary device 202 can detect noises (e.g., with a microphone) that indicate that a conscious activity is being performed by a human. For example, when blinds 210 are opened or closed, blinds 210 can make a distinctive noise that can be detected and identified by primary device 202. Once the noise of blinds 210 opening or closing is identified (e.g., using the sound samples described above), primary device 202 can determine that a conscious human activity has been performed with respect to blinds 210. Similarly, primary device 202 can detect and identify as conscious human activity sounds associated with opening and closing doors, opening and closing drawers, and/or opening and closing windows.

In some implementations, primary device 202 can detect sounds attributable to conscious human activity in bathroom 212. For example, when a human brushes her teeth, turns on a water faucet, takes a shower, or flushes the toilet, these activities create distinctive noises that are attributable to a human (e.g., while a dog can be trained to flush a toilet, this is an unusual activity for a dog). These bathroom noises can be detected and identified by primary device 202, as described above. Once the noise of these bathroom activities are identified, primary device 202 can determine that a conscious human activity has been performed. Similarly, primary device 202 can detect and identify the sound of human footsteps in hallway 214. Once the footsteps are detected and identified, primary device 202 can determine that a conscious human activity has been performed.

In some implementations, primary device 202 can receive indications from secondary devices that a human is awake. For example, the secondary devices can include smart television 220, smart refrigerator 222, smart scale 224, smart oven 226, smart coffee maker 228, and/or a smart personal hygiene device 230 (e.g., electric toothbrush, electric shaver, hairdryer, etc.). The secondary devices can include a computing device 232, such as a laptop computer, smartphone, tablet computer, and/or wearable device. Each of these secondary devices 220-232 can be connected through a network (e.g., Wi-Fi, Bluetooth, etc.) to primary device 202. When used, devices 202-232 can send a message to primary device 202 indicating that the device has been turned on or has received some other conscious interaction from a human. Primary device 202 can interpret a message from the devices 220-232 as evidence of human activity with respect to the corresponding device.

Attributing the Activity to the User

In some implementations, primary device 202 can determine that a detected conscious human activity is attributable to the user of primary device 202. For example, if the user lives alone, all conscious human activity can be attributed to the user. If the user lives with other humans, primary device 202 can determine if the detected conscious human activity should be attributed to the user by identifying the human performing the conscious human activity.

In some implementations, primary device 202 can determine whether the user lives alone by monitoring environmental conditions surrounding primary device 202. For example, primary device 202 can detect noises generated by humans (e.g., breathing, talking, walking, etc.) and determine sounds associated with the user and/or other humans. Each human may have a unique way of walking, talking, breathing, etc., that can be used to distinguish one human from another human. When primary device 202 detects multiple distinct sound patterns associated with different humans, primary device 202 can determine that there are multiple humans present in the house. For example, when primary device 202 detects sleeping sounds and conscious user activity, then primary device 202 can determine that user 204 lives with other humans. When primary device 202 detects sounds (e.g., breathing pattern or other activity) associated with only a single human, then primary device 202 can determine that the user lives alone. If user 204 lives alone, primary device 202 can attribute all conscious human activity to user 204, as described above. If user 204 lives with other humans, primary device 202 can determine whether the detected conscious human activity should be attributed to the user of primary device 202.

Self-Identification

In some implementations, primary device 202 can determine whether a detected conscious human activity should be attributed to the user based on user identification information included in messages received from secondary devices. For example, the user identification information can be a user account identifier (e.g., user name). The user identification information can be a device identifier for a single user device owned by the user. For example, since the single user device can only be operated by a single user who has the log in credentials for the single user account on the device, primary device 202 can attribute each use of the single user device to the owner of the device. Examples of single user devices can include a smartphone, smart watch, smart eye glasses, and the like that operate under a single user account.

In some implementations, primary device 202 can determine whether a detected conscious human activity should be attributed to the user based on user account information. For example, when a human uses one of smart devices 202-230 or computing device 232 (e.g., television, set top box, streaming device, computer, etc.), the human may be required to log into the device. In order to log into the device, the human may provide log in credentials (e.g., account identifier, user identifier, and/or password) that can be used by the device to identify the human using the device. In some implementations, the log in credentials can be received by the device as user input from the human. After the log in credentials are received and the human using the device is identified, the device (e.g., one of smart devices 202-230, or computing device 232) can send the human identification to primary device 202 in a message indicating that a conscious human activity has occurred with respect to the device. Thus, if user 204 logged into the secondary device, primary device 202 can attribute the conscious human activity with respect to the secondary device to user 204.

In some implementations, a secondary device can receive the log in credentials from a single user device, such as a wearable device (e.g., smartwatch 150). For example, a human interacting with smart refrigerator 222 can passively (e.g., without user input) log into smart refrigerator 222 when smart refrigerator 222 detects smart watch 150 associated with a human that is near the smart refrigerator 222. For example, smart watch 150 can automatically transmit information (e.g., over Bluetooth, near field communication "NFC", etc.) to smart refrigerator 222 that can be used by smart refrigerator 222 to identify the human wearing smartwatch 150. After smart refrigerator 222 receives the information identifying the human from smartwatch 150, smart refrigerator 222 can send the identification information to primary device 202 in the message indicating that a conscious human activity has occurred with respect to the smart refrigerator 222. Thus, if user 204 is the owner of the single user device, primary device 202 can attribute the conscious human activity with respect to the secondary device to user 204.

In some implementations, the single user device can notify primary device 202 of conscious user activity with respect to a smart device. For example, since wearable devices are typically single user devices, messages sent through or activities reported by a wearable device can be attributed to the owner of the wearable device. For example, smart watch 150 can receive a signal from smart scale 224 when the wearable device is near smart scale 244. The signal can be received using a short range communication mechanism, such as Bluetooth or NFC, for example. The signal can include information identifying the smart scale 244 and/or a current status of smart scale 244. After smart watch 150 receives the information status information from smart scale 244, smart watch 150 can send the identification information to primary device 202 in a message indicating that a conscious human activity has occurred with respect to the smart scale 244. Smart watch 150 can send the status and identification information received from the smart scale 224 to primary device 202 along with an identifier of the human wearing smart watch 150, for example. Thus, if user 204 is the owner of the single user device (e.g., smart watch 150), primary device 202 can attribute the conscious human activity with respect to the secondary device to user 204.

In some implementations, primary device 202 can determine that user 204 is awake based on location information received from a single user device. For example, the location information can indicate a location relative to an object (e.g., smart device). For example, even if user 204 does not use (e.g., open the door) smart refrigerator 222, the user's proximity to smart refrigerator 222 can indicate that the user is awake since user 204 is not likely to be sleeping when in the kitchen near smart refrigerator 222. When the single user device (e.g., wearable device, smart watch, etc.) reports to primary device 202 that the single user device detected smart refrigerator 222 (e.g., received a NFC or Bluetooth signal from smart refrigerator 222), primary device 202 can determine that user 204 is located in the kitchen and is therefore awake.

Similarly, primary device 202 can receive multiple smart device detection reports from the wearable device over a short period of time. For example, as user 204 moves through the house, the wearable device worn by user 204 can detect smart scale 224, smart refrigerator 222, smart stove 226 and/or smart coffee maker 228 and report these detections to primary device 202. When primary device 202 receives multiple smart device detection reports within a short period of time from the wearable device, primary device 202 can determine that user 204 is moving throughout the house and is not asleep.

Identification Based on Use of Personal Device

Similarly, smart personal hygiene devices (e.g., electric shavers, electric toothbrushes, blow dryers, etc.) can be associated with a single human. For example, while these devices typically do not require a user to log into the devices, most people do not share toothbrushes or electric shavers with other people. When these devices are first used, these smart personal hygiene devices can be paired (e.g., by Bluetooth, NFC, Wi-Fi, etc.) to a computing device (e.g., smartphone, wearable device, other personal computing device, etc.) associated with a single human. When these personal hygiene devices are turned on and used, the personal hygiene device can connect to the paired computing device. If the paired computing device is primary device 202, primary device 202 can determine that user 204 associated with primary device 202 is performing a conscious human activity with respect to the smart personal hygiene device.

Identification Based on Context

In some implementations, primary device 202 can determine whether a detected conscious human activity should be attributed to the user based on context information included in messages received from other devices. For example, when the other devices do not have information identifying the human using the other devices, the other devices can provide context information that can be used by primary device 202 to determine the identity of the human using the device. For example, when a human steps on smart scale 224, smart scale 224 can determine the weight of the human. Smart scale 224 can send the weight measurement to primary device 202. When primary device 202 receives the weight measurement, primary device 202 can compare the new weight measurement to historical weight measurements for the user of primary device 202. If the new weight measurement is similar to prior weight measurements (e.g., the immediately previous weight measurement), then primary device 202 can determine that the user of primary device 202 used smart scale 224. If the new weight measurement is not similar to prior weight measurements, then primary device 202 can determine that the user of primary device 202 is not the human the used smart scale 224.

Similarly, when a human uses a smart media device (e.g., smart television, set top box, streaming media player, etc.), the smart media device can determine the type and/or characteristics of the media that the human is consuming. The smart media device can send the media type (e.g., music, movie, television show, etc.) and/or characteristics (e.g., genre, actors, director, etc.) information to primary device 202. When primary device 202 receives the media information, primary device 202 can compare the media information to historical media preferences data collected for the user of primary device 202. If the media information for the media item currently playing on the smart media device corresponds to the user's historical media preferences, primary device 202 can determine that user 204 is using the smart media device. If the media information for the media item currently playing on the smart media device does not match the user's historical media preferences, primary device 202 can determine that user 204 is not using the smart media device.

Identification Based on Sensor Data

In some implementations, primary device 202 can determine whether a detected human activity should be attributed to the user based on environmental sensor data. For example, a microphone (e.g., sound sensor) can detect sounds associated with human footsteps and/or breathing. Primary device 202 can store historical sound information that includes samples of the user's footsteps while walking on various surfaces (e.g., carpeting, wood floors, concrete, etc.). Primary device 202 can store historical sound information describing the user's walking cadence, for example. Primary device 202 can store historical sound information that includes samples of the user's breathing in various contexts (e.g., while sleeping, walking, sitting, running, etc.). Primary device 202 can compare the detected sounds to the historical sound samples to determine whether the detected sounds should be attributed to the user of primary device 202. For example, when primary device 202 detects footstep sounds and the detected sounds match historical footstep sounds for the user of primary device 202, then primary device 202 can determine that the user is performing a conscious human activity (e.g., walking, running, etc.). When primary device 202 detects breathing sounds associated with an active human activity and the detected breathing sounds match historical breathing sounds for the user of primary device 202, then primary device 202 can determine that the user is performing a conscious human activity. When primary device 202 detects breathing sounds that match historical breathing sounds associated with the user sleeping, then primary device 202 can determine that the user is sleeping. When primary device 202 detects breathing sounds that do not match historical breathing sounds associated with the user sleeping, then primary device 202 can determine that the user is not sleeping.

In some implementations, primary device 202 can receive sensor data from other devices associated with user 204 that indicate user 204 is awake. For example, user 204 can wear a wearable device (e.g., a smartwatch, smart eye glasses, smart contacts, etc.) that includes sensors that can detect heartrate, eye movement, body movement, arm swing, blood pressure, breathing, footsteps, and/or other biometric data about user 204. The wearable device can transmit the sensor data to primary device 202. Primary device 202 can analyze the sensor data to determine whether user 204 is awake or asleep. For example, when the sensor data indicates a lot of body movement (e.g., arm swing, footsteps, fast breathing, etc.), then primary device 202 can determine that user 204 is awake. When the sensor data indicates little body movement, slow deep breathing, rapid eye movement, slow heartrate, etc., then primary device 202 can determine that user 204 is sleeping.

Identification Based on Sleep Status from Other Devices

In some implementations, primary device 202 can determine whether user 204 is performing a conscious human activity based on sleep information received from personal devices of other humans. For example, primary device 202 can determine that the user 204 lives with human 240 and/or human 250 based on detected environmental signals (e.g., breathing sounds, walking sounds, voice sounds, etc.). For example, each person in the house can be associated with unique breathing patterns, walking patterns, and/or voice patterns. Primary device 202 can use these human-specific sounds to distinguish different people living in the house and/or identify the number of people living in the house.

In some implementations, primary device 202 can determine user 204 lives with human 240 and human 250 based on signals received from the personal electronic devices 242 and 252 of human 240 and human 250, respectively. For example, devices 242 and 252 can be configured to determine when their respective users are sleeping in a similar manner to the mechanisms described herein for primary device 202.

In some implementations, primary device 202 can determine which devices belong to user 204 based on information obtained from a service provider account associated with user 204. For example, the service provider can be a media service provider that provides access to applications, movies, music, and/or other media or services. User 204 can register an account with the service provider to gain access to the services provided by the service provider. User 204 can associated primary device 202 and other devices (e.g., a tablet computer, smart watch, wearable device, etc.) belonging to user 204 with the service provider account. Primary device 202 can access the service provider account associated with user 204 and obtain information identifying the devices associated with user 204. Thus, primary device 202 can determine which devices belong to user 204 and which devices belong to other users (e.g., human 240 and/or human 250).

In some implementations, primary device 202 can receive signals from device 242 and/or device 252 indicating the sleep status of human 240 and/or human 252, respectively. For example, primary device 202, personal device 242, and/or personal device 252 can be configured to share sleep status data when the devices are near (e.g., within a threshold distance of) each other. For example, primary device 202, personal device 242, and/or personal device 252 can be configured to transmit sleep status data to other devices that are connected to the same Wi-Fi access point. Primary device 202, personal device 242, and/or personal device 252 can be configured to transmit sleep status data to other devices that connected through a Bluetooth connection or some other near field communication mechanism. Primary device 202, personal device 242, and/or personal device 252 can be configured to transmit sleep status data to other devices that are within a threshold distance of each other (e.g., as determined by a location determining technology, such as a global navigational satellite system, cellular data location system, or Wi-Fi location system).

In some implementations, primary device 202 can determine whether humans other than user 204 are sleeping based on the received sleep status information. For example, primary device 202 can receive sleep status information from personal device 242 and/or personal device 252 that describes the sleep status of human 240 and/or human 250, respectively. When the sleep status data is received, primary device 202 can determine whether human 240 and/or human 250 are sleeping. For example, the sleep status data can indicate whether the human associated with the device is sleeping. Based on the sleep information received from devices 242 and 252, primary device 202 can determine whether user 204 is sleeping. For example, if primary device 202 has determined that three humans are in the house and receives an indication of conscious human activity in the house, primary device 202 can determine that the source of the conscious human activity in the house is user 204 when primary device 202 receives sleep status data from device 242 and device 252 indicating that the other two humans in the house (e.g., human 240 and human 250) are sleeping. If primary device 202 has determined that three humans are in the house and receives an indication of conscious human activity in the house, primary device 202 can determine that the source of the conscious human activity in the house is not user 204 when primary device 202 receives sleep status data from device 242 and/or device 252 indicating that one of the other two humans in the house (e.g., human 240 and human 250) is awake.

In some implementations, primary device 202 can determine that user 204 is awake when the detected conscious human activity can be attributed to user 204. For example, after primary device 202 has detected the conscious human activity, as described above, and has identified user 204 as the source of the conscious human activity, primary device 202 can determine that user 204 is awake. However, when primary device 202 has detected the conscious human activity, as described above, and has identified another human (e.g., other than user 204) as the source of the conscious human activity, primary device 202 can confirm that user 204 is asleep.

Example Process

Figure 3:
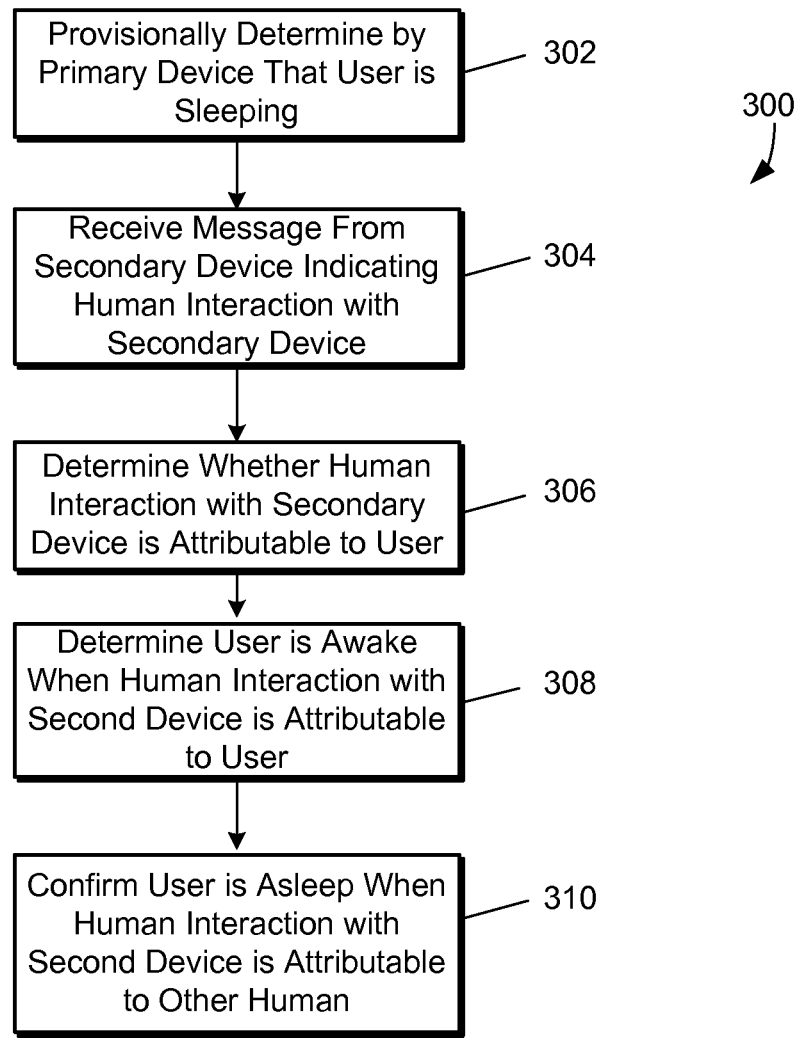
FIG. 3 is flow diagram of an example process for confirming a user of a primary device is asleep.

FIG. 3 is flow diagram of an example process 300 for confirming a user of primary device 202 is asleep. At step 302, primary device 202 can provisionally determine that user 204 is sleeping. For example, primary device 202 can determine that user 204 is sleeping based on primary indicia of user activity. Primary indicia of user activity can be, for example, any active use or input with respect to primary device 202, as described above.

At step 304, primary device 202 can receive a message from a secondary device indicating human interaction with the secondary device. For example, the secondary device can be a household appliance (e.g., smart television, set top box, streaming media player, smart refrigerator, etc.). The secondary device can be a computing device (e.g., a smartphone, tablet computer, laptop computer, etc.). The secondary device can be a wearable device (e.g., smart watch, smart eye glasses, smart contacts, etc.). The message can include state information describing the human interaction with or conscious human use of (e.g., operating context) the secondary device, as described above. For example, the state information can describe whether the secondary device is powered on, which user has logged in to the secondary device, what media is being viewed on the secondary device, or any other information describing the use of the secondary device.

At step 306, primary device 202 can determine whether the human interaction with the secondary device is attributable to the user of primary device 202. For example, primary device 202 can determine whether user 204 is operating the secondary device based on user identification information (e.g., log in information, personal user device information, etc.) received in the message from the secondary device. Primary device 202 can determine whether user 204 is operating the secondary device based on context information received in the message from the secondary device. For example, the context information can describe how the secondary device is being used, what media is being played, sensor data collected by the secondary device, etc. Primary device 202 can compare the context information to historical data related to user 204 to determine whether user 204 is operating the secondary device. For example, when the context information matches the user's music preferences, movie preferences, weight, etc., then primary device 202 can determine that user 204 is operating the secondary device, as described above.

At step 308, primary device 202 can determine that the user is awake when the human interaction with the secondary device is attributable to the user. For example, when primary device 202 can match the identification information or context information to user 204, primary device 202 can determine that the user of primary device 202 is awake.

At step 310, primary device 202 can confirm that the user is asleep when the human interaction with the secondary device is attributable to another human. For example, when primary device 202 is unable to match the identification information or context information to user 204, primary device 202 can determine that another human is using the secondary device and that the user of primary device 202 is asleep.

Figure 4:
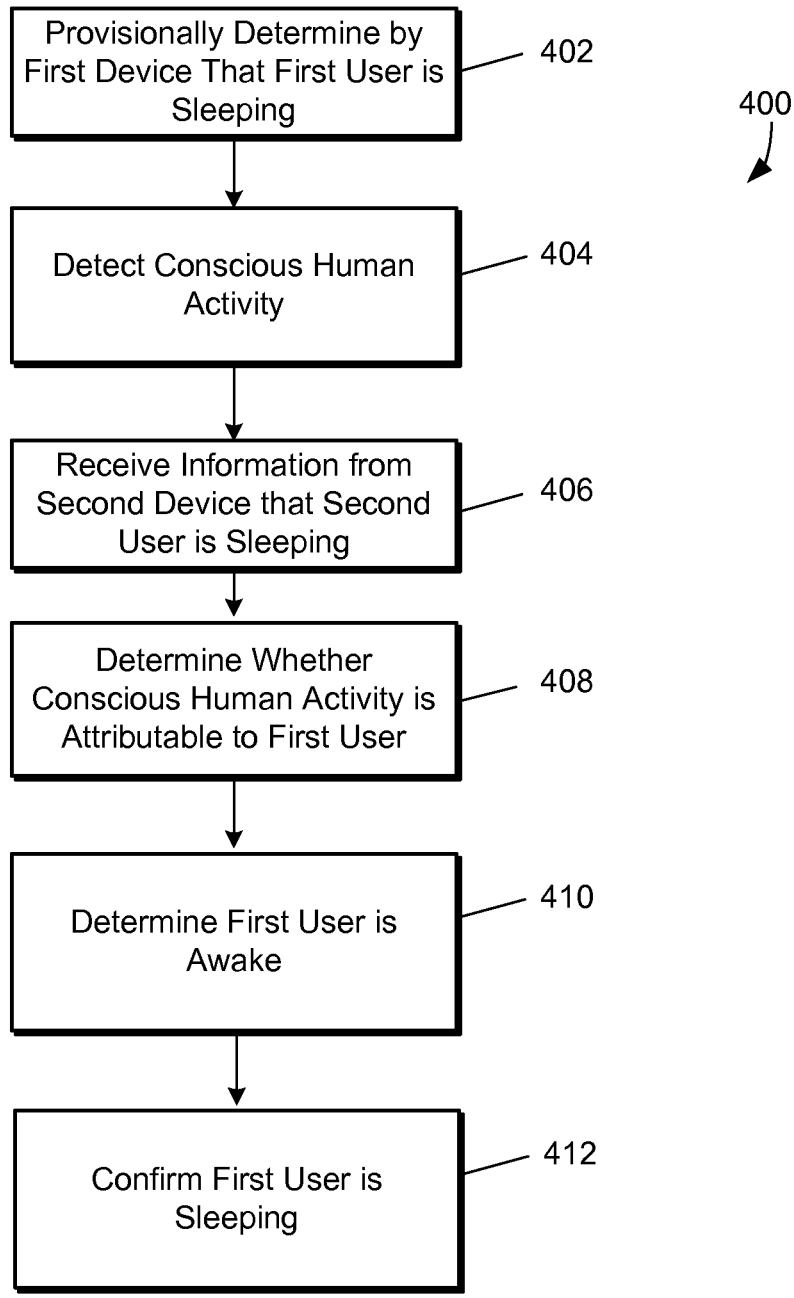
FIG. 4 is a flow diagram of an example process for confirming that a user of a primary device is sleeping based on sleep status data associated with users of other devices.

FIG. 4 is a flow diagram of an example process 400 for confirming that a user of primary device 202 is sleeping based on sleep status data associated with users of other devices. For example, when user 204 of primary device 202 shares a house with other people, primary device 202 will need to determine whether the detected conscious human activity detected by primary device 202 is attributable to user 204 or some other person in the house.

At step 402, primary device 202 can provisionally determine that user 204 is sleeping. For example, primary device 202 can determine that user 204 is sleeping based on primary indicia of user activity. Primary indicia of user activity can be, for example, any active use or input with respect to primary device 202, as described above.

At step 404, primary device 202 can detect conscious human activity. For example, primary device 202 can detect conscious human activity based on sensor data generated by the sensors (e.g., sound sensors, light sensors, motion sensors, etc.) of primary device 202. Primary device 202 can detect conscious human activity based on signals or messages received from other devices, as described above.

At step 406, primary device 202 can receive information from a second device another user is sleeping. For example, the second device can be a primary device of a second user who is not user 204. The second device can be similar to primary device 202 and can be configured to detect and confirm the sleep state of the second user, as described herein with respect to primary device 202. In some implementations, the second device can determine whether the second user is sleeping using the mechanisms described herein and report the second user's sleep state (e.g., sleeping, awake, etc.) to primary device 202.

At step 408, primary device 202 can determine whether the detected conscious human activity is attributable to user 204. For example, if there are two people in the house (e.g., user 204 and the second user) and primary device 202 receives information indicating that the second user is asleep, then primary device 202 can attribute the conscious human activity to user 204. If there are two people in the house (e.g., user 204 and the second user) and primary device 202 receives information indicating that the second user is awake, then primary device 202 can attribute the conscious human activity to the second user.

At step 410, primary device 202 can determine that user 204 is awake. For example, primary device 202 can determine that user 204 is awake based on the determination that the detected conscious human activity is attributable to user 204 at step 408.

At step 412, primary device 202 can confirm that user 204 is sleeping. For example, primary device 202 can determine that user 204 is sleeping based on the determination that the detected conscious human activity is attributable to the second user at step 408.

Figure 5:
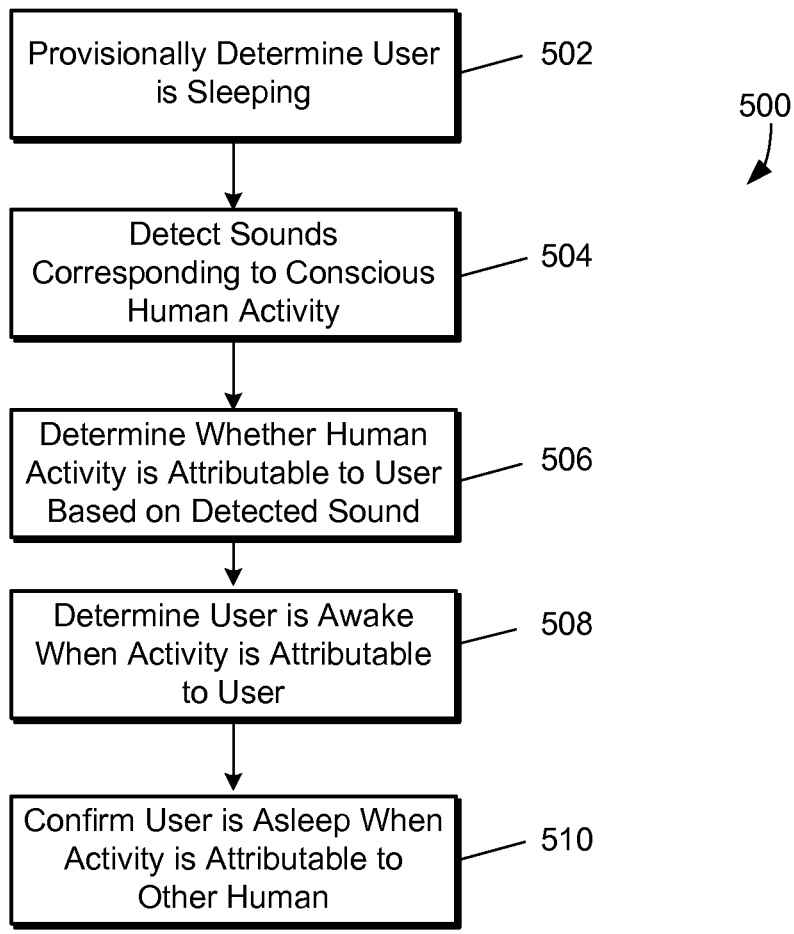
FIG. 5 is a flow diagram of an example process for confirming that a user is sleeping based on the sounds generated by conscious human activity.

FIG. 5 is a flow diagram of an example process 500 for confirming that a user is sleeping based on the sounds generated by conscious human activity. For example, the sounds generated by certain conscious user activities can be uniquely tied to a particular person. For example, a person's voice, footsteps, walking cadence, etc., can be unique and can be used to identify a particular person and/or distinguish one person from another.

At step 502, primary device 202 can provisionally determine that user 204 is sleeping. For example, primary device 202 can determine that user 204 is sleeping based on primary indicia of user activity. Primary indicia of user activity can be, for example, any active use or input with respect to primary device 202, as described above.

At step 504, primary device 202 can detect sounds corresponding to conscious human activity. For example, primary device 202 can be configured with a microphone that can detect sounds generated near primary device 202. Some of the detected sounds can be generated by conscious human activity (e.g., walking, talking, brushing teeth, taking a shower, opening a door, etc.).

At step 506, primary device 202 can determine whether the conscious human activity is attributable to user 204 based on the detected sound. For example, the detected sounds of conscious user activity can be analyzed to identify a person who is performing the activity. For example, a person's voice can be used to identify the person speaking. The pattern or cadence of foot falls when a person walks can be used to identify the person walking. A person may brush their teeth in a particular way (e.g., pattern) that can be used to identify the person brushing their teeth. Primary device 202 collect and can store these sound patterns associated with user 204 and use the sound patterns to later identify user 204 or distinguish activities performed by user 204 from activities performed by other people. For example, primary device 202 can compare a detected sound (or pattern of sounds) of conscious human activity to the stored sounds associated with user 204. If the detected sounds match at least one of the stored sounds associated with user 204, primary device 202 can determine that the conscious human activity is attributable to user 204. If the detected sounds do not match at least one of the stored sounds associated with user 204, primary device 202 can determine that the conscious human activity is attributable to some other person.

At step 508, primary device 202 can determine that user 204 is awake when the conscious human activity is attributable to user 204. For example, when primary device 202 determines that the detected sound of conscious human activity is attributable to user 204 at step 506, primary device 202 can determine that user 204 is awake.

At step 510, primary device 202 can determine that user 204 is awake when the conscious human activity is attributable to user 204. For example, when primary device 202 determines that the detected sound of conscious human activity is attributable to another person at step 506, primary device 202 can confirm that user 204 is sleeping.

Figure 6:
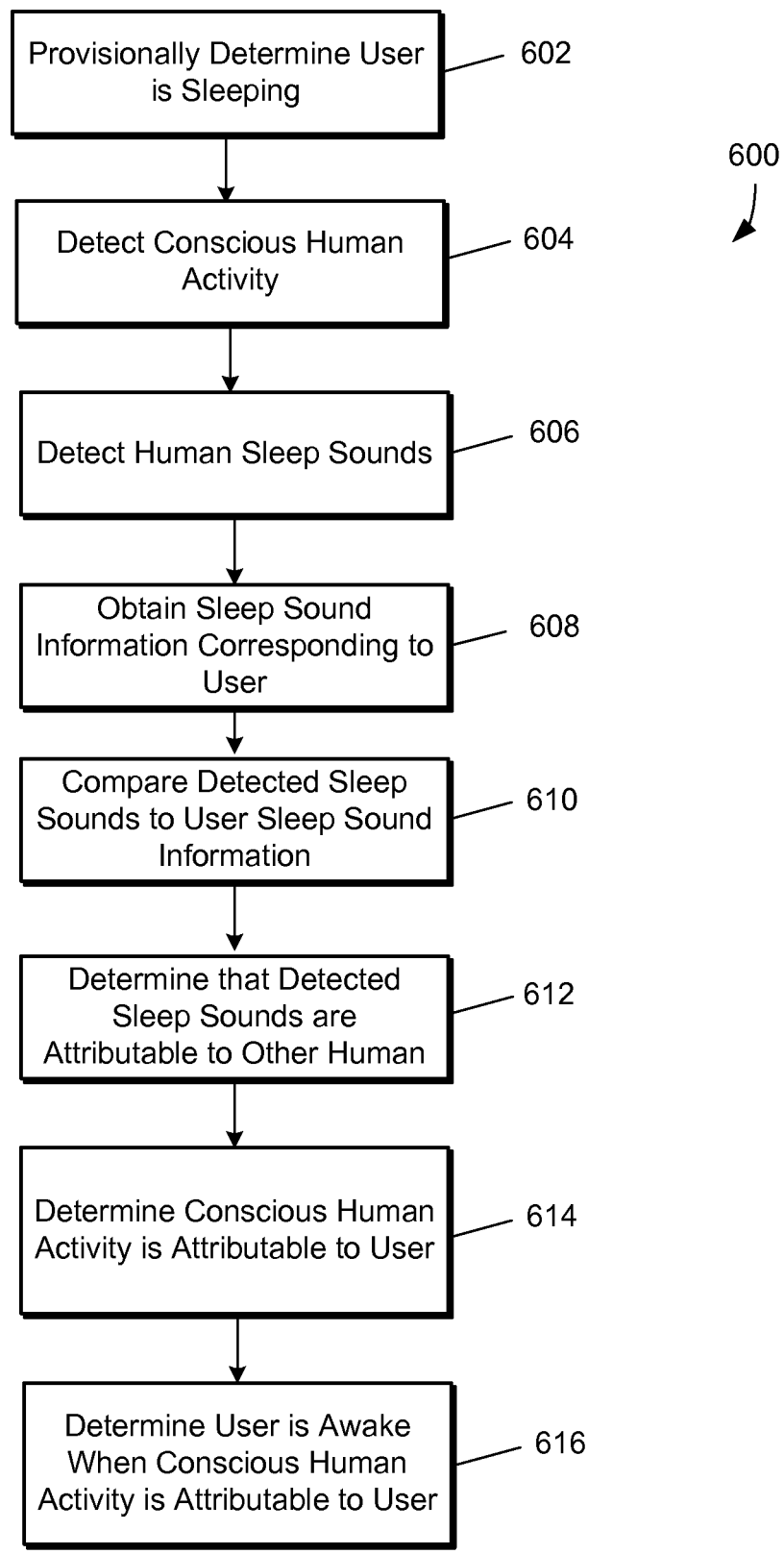
FIG. 6 is a flow diagram of an example process for determining that a user is awake based on sleep sounds generated by other people.

FIG. 6 is a flow diagram of an example process 600 for determining that user 204 is awake based on sleep sounds generated by other people. For example, some computing devices can detect sleep sounds (e.g., slow breathing, deep breathing, snoring, etc.) generated by a person sleeping alone in a room and determine based on the sleep sounds that the person is sleeping. However, when multiple people share a room for sleeping, it may be difficult to determine who is sleeping and who is awake. The computing device may be able to determine based on the sleep noises that someone is sleeping but may not be able to identify who is sleeping. Thus, in some implementations, primary device 202 can be configured to distinguish between user 204 sleeping and other people sleeping based on detected sleep noises. The description of process 600 below describes a scenario where primary device 202 determines which of two people who share a room are sleeping, however process 600 can be applied to situations where more than two people share a room.

At step 602, primary device 202 can provisionally determine that user 204 is sleeping. For example, primary device 202 can determine that user 204 is sleeping based on primary indicia of user activity. Primary indicia of user activity can be, for example, any active use or input with respect to primary device 202, as described above.

At step 604, primary device 202 can detect conscious human activity. For example, primary device 202 can detect conscious user activity based on sensor data and/or information obtained from other devices, as described above. However, when multiple people share a home, primary device 202 must determine whether user 204 or some other person is responsible for the conscious human activity.

At step 606, primary device 202 can detect human sleep sounds. For example, when primary device 202 provisionally determines that user 204 is sleeping, primary device 202 can turn on the microphone of primary device 202 to monitor and/or detect noises near primary device 202. For example, primary device 202 can detect the sounds of sleep made by people sleeping near primary device 202. For example, user 204 may be married or have a roommate and primary device 202 may detect the sleep noises generated by user 204 and/or the other person.

At step 608, primary device 202 can obtain sleep sound information corresponding to user 204. For example, over time primary device 202 can record sleep sounds while user 204 is sleeping and generate samples (e.g., fingerprints) of the sounds of user 204 sleeping. Primary device 202 can store the sleep sound samples and use the sleep sounds samples to later identify user 204, as described below. If user 204 typically shares a room with another person, primary device 202 can determine which sleep sounds correspond to user 204 based on frequency of detection and similarity of sounds. For example, since primary device 202 is the personal device of user 204, primary device 202 will detect sleep sounds associated with user 204 more frequently than the sleep sounds of other people (e.g., sometimes user 204 will sleep alone). Thus, to determine which sleep sounds correspond to user 204 and to filter out sleep sounds generated by other people, primary device can generate groups of sleep sound samples based on similarity of sound and determine the frequency of occurrence of the sleep sounds in each group. The group with the highest frequency (or highest number of instances) of sleep sound samples will most likely correspond to user 204. This group can be the sleep sound information (e.g., sample set) used to identify sleep sounds of user 204.

At step 610, primary device 202 can compare detected sleep sounds to the sleep sound information for user 204. After primary device 202 obtains the sleep sound information (e.g., sleep sound samples) for user 204, primary device 202 can compare the detected sleep sounds to the sleep sound information to determine whether the detected sleep sounds match (e.g., are similar to) the sleep sound samples recorded for user 204.

At step 612, primary device 202 can determine that the detected sleep sounds are attributable to another human. For example, when the detected sleep sounds do not match the sleep sound information for user 204, primary device 202 can determine that the sleep sounds were generated by another person (e.g., spouse, roommate, etc.) sleeping near primary device 202.

At step 614, primary device 202 can determine that the conscious human activity is attributable to user 204. For example, when there are only two people sharing a room or a home, primary device 202, through a process of elimination, can determine the conscious human activity is attributable to user 204 because the other person in the house is asleep.

At step 616, primary device 202 can determine that user 204 is awake when the conscious human activity is attributable to the user. For example, user 204 cannot performing the conscious human activity when user 204 is asleep.

Thus, primary device 202 can perform processes 300-600 to confirm (or disprove) the provisional sleep determination based on secondary indicia of user activity. Each of the processes described above may be performed individually or in combination to confirm whether the user of primary device 202 is actually asleep. For example, sensor data may be used in combination with secondary device data to determine whether user 204 is awake or asleep. While the steps of each process 300-600 are presented in a particular order for ease of explanation, the order in which the steps are performed may be changed or rearranged while still producing similar results.

Example System Architecture

Figure 7:
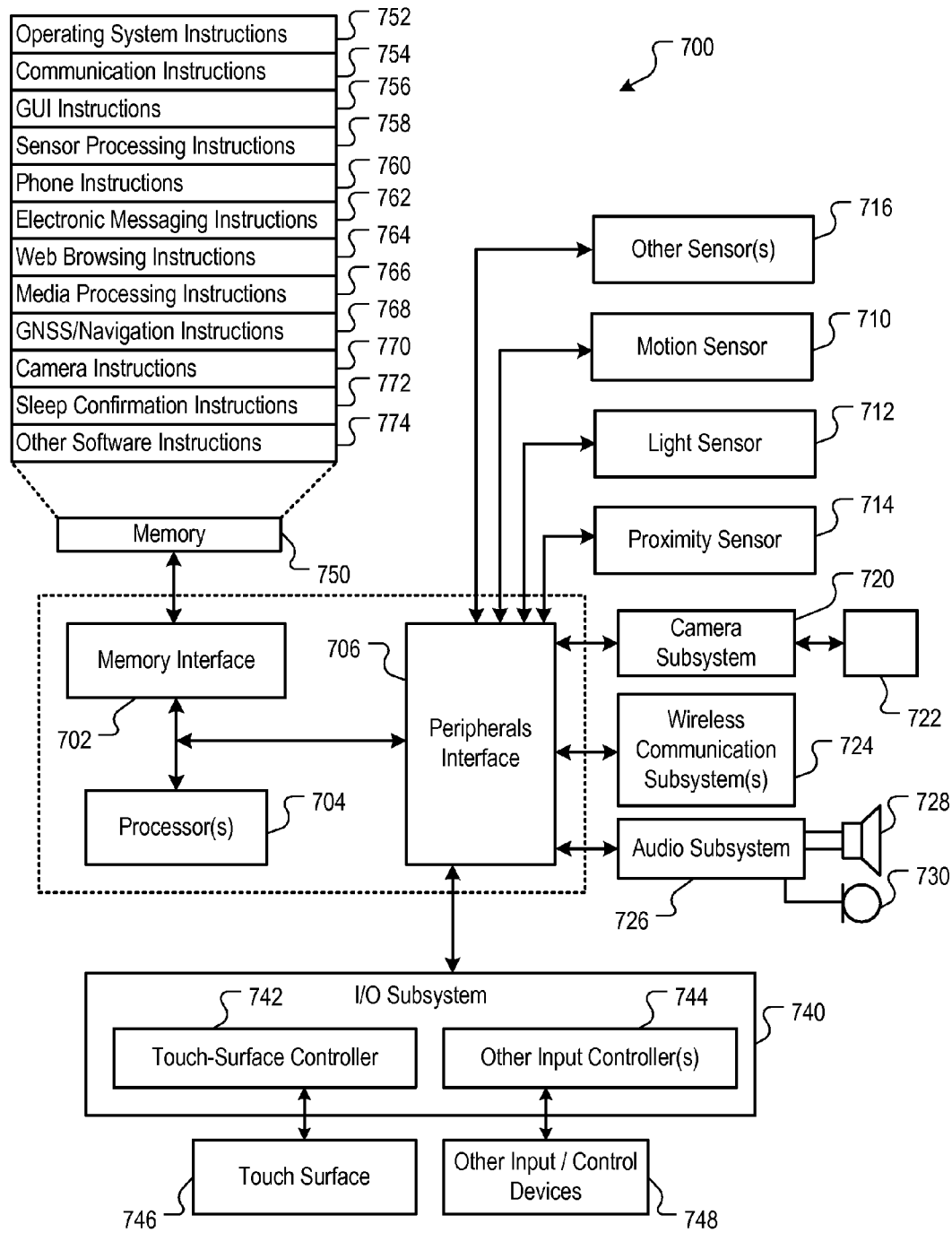
FIG. 7 is a block diagram of an example computing device 700 that can implement the features and processes of FIGS. 1-6.

FIG. 7 is a block diagram of an example computing device 700 that can implement the features and processes of FIGS. 1-6. The computing device 700 can include a memory interface 702, one or more data processors, image processors and/or central processing units 704, and a peripherals interface 706. The memory interface 702, the one or more processors 704 and/or the peripherals interface 706 can be separate components or can be integrated in one or more integrated circuits. The various components in the computing device 700 can be coupled by one or more communication buses or signal lines.

Sensors, devices, and subsystems can be coupled to the peripherals interface 706 to facilitate multiple functionalities. For example, a motion sensor 710, a light sensor 712, and a proximity sensor 714 can be coupled to the peripherals interface 706 to facilitate orientation, lighting, and proximity functions. Other sensors 716 can also be connected to the peripherals interface 706, such as a global navigation satellite system (GNSS) (e.g., GPS receiver), a temperature sensor, a biometric sensor, magnetometer or other sensing device, to facilitate related functionalities.

A camera subsystem 720 and an optical sensor 722, e.g., a charged coupled device (CCD) or a complementary metal-oxide semiconductor (CMOS) optical sensor, can be utilized to facilitate camera functions, such as recording photographs and video clips. The camera subsystem 720 and the optical sensor 722 can be used to collect images of a user to be used during authentication of a user, e.g., by performing facial recognition analysis.

Communication functions can be facilitated through one or more wireless communication subsystems 724, which can include radio frequency receivers and transmitters and/or optical (e.g., infrared) receivers and transmitters. The specific design and implementation of the communication subsystem 724 can depend on the communication network(s) over which the computing device 700 is intended to operate. For example, the computing device 700 can include communication subsystems 724 designed to operate over a GSM network, a GPRS network, an EDGE network, a Wi-Fi or WiMax network, and a Bluetooth™ network. In particular, the wireless communication subsystems 724 can include hosting protocols such that the device 100 can be configured as a base station for other wireless devices.

An audio subsystem 726 can be coupled to a speaker 728 and a microphone 730 to facilitate voice-enabled functions, such as speaker recognition, voice replication, digital recording, and telephony functions. The audio subsystem 726 can be configured to facilitate processing voice commands, voiceprinting and voice authentication, for example.

The I/O subsystem 740 can include a touch-surface controller 742 and/or other input controller(s) 744. The touch-surface controller 742 can be coupled to a touch surface 746. The touch surface 746 and touch-surface controller 742 can, for example, detect contact and movement or break thereof using any of a plurality of touch sensitivity technologies, including but not limited to capacitive, resistive, infrared, and surface acoustic wave technologies, as well as other proximity sensor arrays or other elements for determining one or more points of contact with the touch surface 746.

The other input controller(s) 744 can be coupled to other input/control devices 748, such as one or more buttons, rocker switches, thumb-wheel, infrared port, USB port, and/or a pointer device such as a stylus. The one or more buttons (not shown) can include an up/down button for volume control of the speaker 728 and/or the microphone 730.

In one implementation, a pressing of the button for a first duration can disengage a lock of the touch surface 746; and a pressing of the button for a second duration that is longer than the first duration can turn power to the computing device 700 on or off. Pressing the button for a third duration can activate a voice control, or voice command, module that enables the user to speak commands into the microphone 730 to cause the device to execute the spoken command. The user can customize a functionality of one or more of the buttons. The touch surface 746 can, for example, also be used to implement virtual or soft buttons and/or a keyboard.

In some implementations, the computing device 700 can present recorded audio and/or video files, such as MP3, AAC, and MPEG files. In some implementations, the computing device 700 can include the functionality of an MP3 player, such as an iPod™. The computing device 700 can, therefore, include a 36-pin connector that is compatible with the iPod. Other input/output and control devices can also be used.

The memory interface 702 can be coupled to memory 750. The memory 750 can include high-speed random access memory and/or non-volatile memory, such as one or more magnetic disk storage devices, one or more optical storage devices, and/or flash memory (e.g., NAND, NOR). The memory 750 can store an operating system 752, such as Darwin, RTXC, LINUX, UNIX, OS X, WINDOWS, or an embedded operating system such as VxWorks.

The operating system 752 can include instructions for handling basic system services and for performing hardware dependent tasks. In some implementations, the operating system 752 can be a kernel (e.g., UNIX kernel). For example, operating system 752 can implement the sleep confirmation features as described with reference to FIGS. 1-6.

The memory 750 can also store communication instructions 754 to facilitate communicating with one or more additional devices, one or more computers and/or one or more servers. The memory 750 can include graphical user interface instructions 756 to facilitate graphic user interface processing; sensor processing instructions 758 to facilitate sensor-related processing and functions; phone instructions 760 to facilitate phone-related processes and functions; electronic messaging instructions 762 to facilitate electronic-messaging related processes and functions; web browsing instructions 764 to facilitate web browsing-related processes and functions; media processing instructions 766 to facilitate media processing-related processes and functions; GNSS/Navigation instructions 768 to facilitate GNSS and navigation-related processes and instructions; and/or camera instructions 770 to facilitate camera-related processes and functions.

The memory 750 can store other software instructions 772 to facilitate other processes and functions, such as the sleep confirmation processes and functions as described with reference to FIGS. 1-6.

The memory 750 can also store other software instructions 774, such as web video instructions to facilitate web video-related processes and functions; and/or web shopping instructions to facilitate web shopping-related processes and functions. In some implementations, the media processing instructions 766 are divided into audio processing instructions and video processing instructions to facilitate audio processing-related processes and functions and video processing-related processes and functions, respectively.

Each of the above identified instructions and applications can correspond to a set of instructions for performing one or more functions described above. These instructions need not be implemented as separate software programs, procedures, or modules. The memory 750 can include additional instructions or fewer instructions. The instructions can be executed by processor(s) 704, for example, to perform the various processes and functions described above. Furthermore, various functions of the computing device 700 can be implemented in hardware and/or in software, including in one or more signal processing and/or application specific integrated circuits.

What is claimed is:

1. A method for providing a sleep determination for a user with a first computing device programmed to perform the method, comprising:
    provisionally determining, by the first computing device, that the user of the first computing device is sleeping based on data indicating that the user is not currently using the first computing device to provide a provisional determination that the user is sleeping;
    receiving, by the first computing device, a communication from a second device indicating that conscious human activity is being performed with respect to the second device that is unrelated to the first computing device, wherein the communication includes a second identifier that identifies a user account corresponding to an operator of the second device;
    comparing, by the first computing device, the second identifier received from the second computing device to a first identifier that identifies a user account corresponding to the user of the first computing device;
    determining, by the first computing device, whether the conscious human activity is being performed by the user of the first computing device based on the comparison of the first identifier and the second identifier; and
    revising, by the first computing device, the provisional determination that the user is sleeping to indicate that the user is awake in response to a determination that the conscious human activity is being performed by the user of the first computing device in order to provide a more accurate sleep determination for the user.

2. The method of claim 1, further comprising:
    confirming, by the first computing device, that the user is sleeping in response to a determination that the conscious human activity is being performed by someone other than the user of the first computing device.

3. The method of claim 1, further comprising:
    detecting, by the first computing device, sounds generated by second conscious human activity;
    determining, by the first computing device, that the detected sounds correspond to the user of the first computing device; and
    determining, by the first computing device, that the second conscious human activity is being performed by the user of the first computing device in response to a determination that the detected sounds correspond to the user of the first computing device.

4. The method of claim 1, further comprising:
    detecting, by the first computing device, sounds generated by second conscious human activity;
    determining, by the first computing device, that the detected sounds are inconsistent with sounds associated with the user of the first computing device; and
    determining, by the first computing device, that the second conscious human activity is being performed by someone other than the user of the first computing device in response to a determination that the detected sounds are inconsistent with sounds associated with the user of the first computing device.

5. The method of claim 1, further comprising:
    detecting, by the first computing device, sleep sounds generated by unconscious human activity;
    determining, by the first computing device, whether the sleep sounds are being performed by the user of the first computing device; and
    maintaining, by the first computing device, the provisional determination that the user is sleeping in response to a determination that the sleep sounds are being performed by the user of the first computing device.

6. The method of claim 1, further comprising determining that the second device is a personal device of the user of the first computing device, and
    wherein the determining whether the conscious human activity is being performed by the user of the first computing device further comprises determining, by the first computing device, that the conscious human activity is being performed by the user of the first computing device in response to the second device being the personal device of the user.

7. The method of claim 1, wherein the communication from the second device further indicates that the conscious human activity is being performed with respect to a third device.

8. The method of claim 7, wherein the conscious human activity is positioning of the second device within communications range of the third device.

9. A non-transitory computer-readable medium including one or more sequences of instructions that, when executed by one or more processors, causes:
    provisionally determining, by a first computing device, that a user of the first computing device is sleeping based on data indicating that the user is not currently using the first computing device to provide a provisional determination that the user is sleeping;
    receiving, by the first computing device, a communication from a second device indicating that conscious human activity is being performed with respect to the second device that is unrelated to the first computing device, wherein the communication includes a second identifier that identifies a user account corresponding to an operator of the second device;
    comparing, by the first computing device, the second identifier received from the second computing device to a first identifier that identifies a user account corresponding to the user of the first computing device;
    determining, by the first computing device, whether the conscious human activity is being performed by the user of the first computing device based on the comparison of the first identifier and the second identifier; and
    revising, by the first computing device, the provisional determination that the user is sleeping to indicate that the user is awake in response to a determination that the conscious human activity is being performed by the user of the first computing device in order to provide a more accurate sleep determination for the user.

10. The non-transitory computer-readable medium of claim 9, wherein the instructions cause:

confirming, by the first computing device, that the user is sleeping in response to a determination that the conscious human activity is being performed by someone other than the user of the first computing device.

11. The non-transitory computer-readable medium of claim 9, wherein the instructions cause:
   detecting, by the first computing device, sounds generated by second conscious human activity;
   determining, by the first computing device, that the detected sounds correspond to the user of the first computing device; and
   determining, by the first computing device, that the second conscious human activity is being performed by the user of the first computing device in response to a determination that the detected sounds correspond to the user of the first computing device.

12. The non-transitory computer-readable medium of claim 9, wherein the instructions cause:
   detecting, by the first computing device, sounds generated by second conscious human activity;
   determining, by the first computing device, that the detected sounds are inconsistent with sounds associated with the user of the first computing device; and
   determining, by the first computing device, that the second conscious human activity is being performed by someone other than the user of the first computing device in response to a determination that the detected sounds are inconsistent with sounds associated with the user of the first computing device.

13. The non-transitory computer-readable medium of claim 9, wherein the instructions cause:
   detecting, by the first computing device, sleep sounds generated by unconscious human activity;
   determining, by the first computing device, whether the sleep sounds are being performed by the user of the first computing device; and
   maintaining, by the first computing device, the provisional determination that the user is sleeping in response to a determination that the sleep sounds are being performed by the user of the first computing device.

14. The non-transitory computer-readable medium of claim 9, wherein the instructions cause:
   determining that the second device is a personal device of the user of the first computing device, and
   wherein the determining whether the conscious human activity is being performed by the user of the first computing device further comprises determining, by the first computing device, that the conscious human activity is being performed by the user of the first computing device in response to the second device being the personal device of the user.

15. The non-transitory computer-readable medium of claim 9, wherein the communication from the second device further indicates that the conscious human activity is being performed with respect to a third device.

16. The non-transitory computer-readable medium of claim 15, wherein the conscious human activity is positioning of the second device within communications range of the third device.

17. A system comprising:
   one or more processors; and
   a non-transitory computer-readable medium including one or more sequences of instructions that, when executed by the one or more processors, causes:
      provisionally determining, by a first computing device, that a user of the first computing device is sleeping based on data indicating that the user is not currently using the first computing device to provide a provisional determination that the user is sleeping;
      receiving, by the first computing device, a communication from a second device indicating that conscious human activity is being performed with respect to the second device that is unrelated to the first computing device, wherein the communication includes a second identifier that identifies a user account corresponding to an operator of the second device;
      comparing, by the first computing device, the second identifier received from the second computing device to a first identifier that identifies a user account corresponding to the user of the first computing device;
      determining, by the first computing device, whether the conscious human activity is being performed by the user of the first computing device based on the comparison of the first identifier and the second identifier; and
      revising, by the first computing device, the provisional determination that the user is sleeping to indicate that the user is awake in response to a determination that the conscious human activity is being performed by the user of the first computing device in order to provide a more accurate sleep determination for the user.

18. The system of claim 17, wherein the instructions cause:
   confirming, by the first computing device, that the user is sleeping in response to a determination that the conscious human activity is being performed by someone other than the user of the first computing device.

19. The system of claim 17, wherein the instructions cause:
   detecting, by the first computing device, sounds generated by second conscious human activity;
   determining, by the first computing device, that the detected sounds correspond to the user of the first computing device; and
   determining, by the first computing device, that the second conscious human activity is being performed by the user of the first computing device in response to a determination that the detected sounds correspond to the user of the first computing device.

20. The system of claim 17, wherein the instructions cause:
   detecting, by the first computing device, sounds generated by second conscious human activity;
   determining, by the first computing device, that the detected sounds are inconsistent with sounds associated with the user of the first computing device; and
   determining, by the first computing device, that the second conscious human activity is being performed by someone other than the user of the first computing device in response to a determination that the detected sounds are inconsistent with sounds associated with the user of the first computing device.

21. The system of claim 17, wherein the instructions cause:
   detecting, by the first computing device, sleep sounds generated by unconscious human activity;
   determining, by the first computing device, whether the sleep sounds are being performed by the user of the first computing device; and maintaining, by the first computing device, the provisional determination that the user is sleeping in response to a determination that the sleep sounds are being performed by the user of the first computing device.

22. The system of claim 17, wherein the instructions cause:
   determining that the second device is a personal device of the user of the first computing device, and
   wherein the determining whether the conscious human activity is being performed by the user of the first computing device further comprises determining, by the first computing device, that the conscious human activity is being performed by the user of the first computing device in response to the second device being the personal device of the user.

23. The system of claim 17, wherein the communication from the second device further indicates that the conscious human activity is being performed with respect to a third device.

24. The system of claim 23, wherein the conscious human activity is positioning of the second device within communications range of the third device.

* * * * *